Feb. 18, 1936. C. N. MOORE Plant Pat. 165

REGAL LILY

Filed Oct. 16, 1934

Inventor:
Chester N. Moore,
by Harry E. Dunham
His Attorney.

Patented Feb. 18, 1936

Plant Pat. 165

UNITED STATES PATENT OFFICE

165

REGAL LILY

Chester N. Moore, Schenectady, N. Y., assignor to General Electric Company, a corporation of New York Application October 16, 1934, Serial No. 748,534

1 Claim. (Cl. 47—60)

My new variety of regal lily (Lilium Regale) is an improvement over the ordinary regal lily in the anther of which a profusion of yellow pollen is produced which drops on the petals during the blooming period.

It is the object of my invention to produce a new variety of lily in which the anthers are non-dehiscent and therefore do not shed pollen which would discolor the white petals of the flowers. In the new variety of regal lily produced by me the bright canary yellow color is practically absent in the throat of the calyx of the blossom.

The herein described new regal lily is a mutation which resulted when a number of lily bulbs were subjected to the following treatment prior to planting. The bulbs treated were regular commercial bulbs of a pure strain of regal lily and, it is believed, had been exposed to no previous influences which would be likely to affect the character of their reproduction. The bulbs while on a backing of sheet lead were exposed for about ½ minute to X-rays from a tungsten-target water-cooled X-ray tube of the thick-walled type supplied with energy from a source which furnished a peak voltage of 200 kilovolts and a current of 30 milliamperes, and the focal distance was about 50 centimeters. Some of the bulbs thus treated produced flowers such as illustrated in the accompanying drawing. These bulbs were found to be capable of asexual reproduction from bulblets derived from the original plant, the novel characteristics of the parent lily persisting in the lilies thus reproduced.

Figure 1:
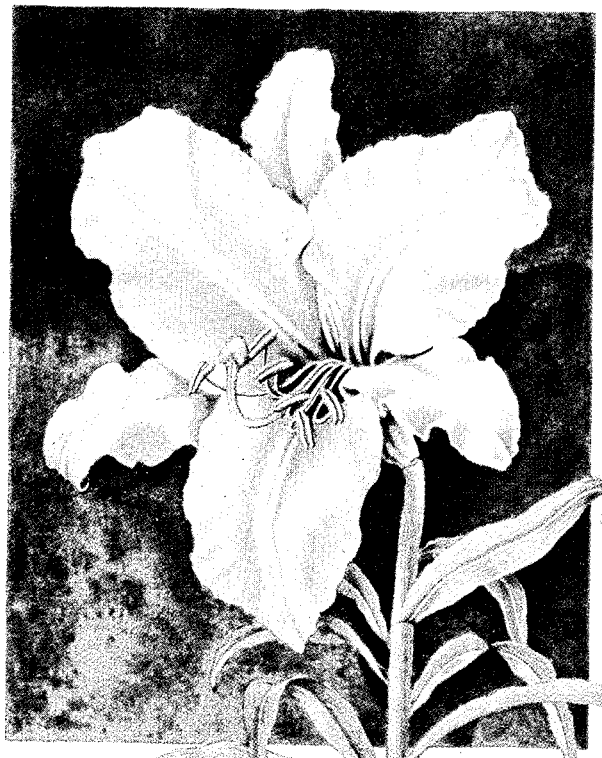
Figure 2:
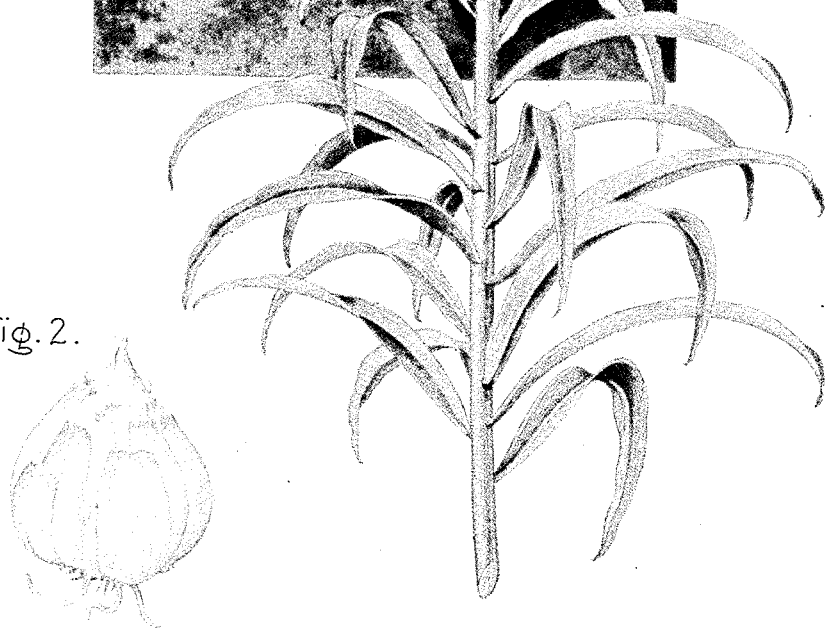

The accompanying drawing shows in approximately natural size in Fig. 1 a portion of the stalk, leaves, and the blossom of a lily produced in accordance with my invention. Fig. 2 is a perspective view of a bulb of regal lily such as was subjected to X-ray treatment, and thereafter asexually reproduced.

The following is a detailed description of this new regal lily:

*Bulb.*—The bulb of my new variety of lily is composed of large fleshy overlapping scales as in the well known ordinary forms of regal lily.

*Leaves and stems.*—The dark green, long, slender leaves of my new variety of lily are borne on a stout, erect stem, as in the well known ordinary forms of regal lily.

*Flower.*—The flowers of my new variety of lily are large, trumpet-shaped, the six waxy petals being practically white on the inside, the three outer ones being shaded with pink and purple on the outside. The petals are similar in size and shape to those of the well known ordinary form of regal lily. They are characterized, however, by the almost complete absence of yellow color at the inside of the base of the petals.

As illustrated in the drawing, there is a slight yellowish color at the base of the midrib of the petals.

A characteristic feature of my new regal lily is the behavior of the anthers, which, as they develop after the opening of the flower, fail to dehisce, thus preventing the shedding of the pollen. The anthers shrink in size, change in color from orange to a reddish brown (Dictionary of Color, Maerz and Paul, 5-F-11) and add to the beauty of the flower if allowed to remain attached to the filament during the life of the flower.

That the new material actually represents a distinct and reproducible variety of its genus is evidenced by the fact that all bulblets developed to the flowering stage from treated parent bulb have uniformly produced flowers having the characteristics described and claimed herein.

What I claim as new and desire to secure by Letters Patent of the United States, is:

The variety of regal lily herein shown and described characterized by the fact that its anthers are non-dehiscent, turning from an original orange tint to a reddish-brown color and shrinking in size throughout the blooming period of the flower, and by the fact that the throat of the flower is very lightly tinted with yellow the petals otherwise being substantially white.

CHESTER N. MOORE.